United States Patent
Stenzler et al.

(10) Patent No.: US 10,335,567 B2
(45) Date of Patent: Jul. 2, 2019

(54) NITRIC OXIDE UPPER AIRWAY DELIVERY SYSTEM AND METHOD

(71) Applicant: 12th Man Technologies, Inc., Garden Grove, CA (US)

(72) Inventors: Alex Stenzler, Long Beach, CA (US); Steve Han, Huntington Beach, CA (US)

(73) Assignee: 12th Man Technologies, Inc., Garden Grove, CA (US)

( * ) Notice: Subject to any disclaimer, the term of this patent is extended or adjusted under 35 U.S.C. 154(b) by 72 days.

(21) Appl. No.: 14/011,326

(22) Filed: Aug. 27, 2013

(65) Prior Publication Data

US 2015/0065904 A1    Mar. 5, 2015

(51) Int. Cl.

| | | |
|---|---|---|
| *A61M 16/06* | (2006.01) | |
| *A61B 7/00* | (2006.01) | |
| *A61M 16/20* | (2006.01) | |
| *A61M 15/08* | (2006.01) | |
| *A61M 16/10* | (2006.01) | |
| *A61M 16/12* | (2006.01) | |
| *A61B 5/00* | (2006.01) | |
| *A61M 16/00* | (2006.01) | |
| *A61M 15/00* | (2006.01) | |
| *A61B 5/087* | (2006.01) | |

(52) U.S. Cl.
CPC ......... *A61M 16/0666* (2013.01); *A61B 7/003* (2013.01); *A61M 15/08* (2013.01); *A61M 16/10* (2013.01); *A61M 16/202* (2014.02); *A61B 5/087* (2013.01); *A61B 5/6819* (2013.01); *A61M 15/0098* (2014.02); *A61M 16/107* (2014.02); *A61M 16/12* (2013.01); *A61M 2016/0021* (2013.01); *A61M 2016/0024* (2013.01); *A61M 2016/0027* (2013.01); *A61M 2016/0033* (2013.01); *A61M 2016/1035* (2013.01); *A61M 2202/0275* (2013.01); *A61M 2205/3375* (2013.01); *A61M 2210/0681* (2013.01)

(58) Field of Classification Search
CPC .......... A61M 15/08; A61M 2202/0275; A61M 2016/0021; A61M 2016/0024; A61M 2210/0681; A61M 2016/0033; A61M 15/0098; A61M 2205/3375; A61M 16/12; A61B 7/003; A61B 5/0878; A61B 5/087; A61B 5/6819
USPC ................ 600/537, 538; 128/203.14, 203.22
See application file for complete search history.

(56) References Cited

U.S. PATENT DOCUMENTS

| | | |
|---|---|---|
| 6,432,077 B1 | 8/2002 | Stenzler |
| 6,581,599 B1 | 6/2003 | Stenzler |
| 6,793,644 B2 | 9/2004 | Stenzler |

(Continued)

OTHER PUBLICATIONS

Fraenkel et al., "Lower airway inflammation during rhinovirus colds in normal and in asthmatic subjects" Am. J. Respir. Crit. Care Med. 1995: 151:879-886.

(Continued)

*Primary Examiner* — Peter S Vasat
*Assistant Examiner* — Margaret M Luarca
(74) *Attorney, Agent, or Firm* — Riverside Law LLP (57) ABSTRACT

The present invention provides a system and method for delivery of nitric oxide to the upper respiratory tract without resulting in nitric oxide delivery to the lungs. In certain embodiments, the invention comprises the use of a flow sensor to sense the exhalation of the subject, and delivering a nitric oxide containing gas upon sensed exhalation.

22 Claims, 3 Drawing Sheets

(56) References Cited

U.S. PATENT DOCUMENTS

| | | | |
|---|---|---|---|
| 7,220,393 B2 | 5/2007 | Miller | |
| 7,560,076 B2 | 7/2009 | Rounbehler | |
| 7,939,045 B2 | 5/2011 | Miller | |
| 8,043,252 B2 | 10/2011 | Miller | |
| 2005/0074506 A1* | 4/2005 | Natan et al. | 424/718 |
| 2005/0217679 A1* | 10/2005 | Miller et al. | 128/207.18 |
| 2008/0142002 A1* | 6/2008 | Fink et al. | 128/200.14 |
| 2013/0072755 A1* | 3/2013 | Papania | A61M 11/005 600/109 |

OTHER PUBLICATIONS

Gern J.E., "Viral respiratory infection and the link to asthma," Pediatr. Infect. Dis. J. 2004; 23 (Suppl. 1): S78-S86.
Miller et al.,"Innate Protection of *Mycobacterium smegmatis* against the Antimicrobial Activity of Nitric Oxide Is Provided by Mycothiol" Antimicrobial Agents and Chemotherapy 2007, 51 (9); 3364-66.
Papadopoulos et al., "Rhinoviruses infect the lower airways" J Infect Dis 2000; 181:1875-1884.
Pizzichini et al., "Asthma and Natural Colds. Inflammatory Indices in Induced Sputum: A Feasibility Study," Am J Respir Crit Care Med 1998; 158:1178.
Rimmelzwaan et al., "Inhibition of Influenza Virus Replication by Nitric Oxide" J Virol 1999; 73:8880-83.
Rodriguez and Teste "The Nasal Route as a Potential Pathway for Delivery of Erythroproietin in the Treatment of Acute Ischemic Stroke in Humans" The Scientific World Journal 2009, 9:970-981.
Sanders et al., "Role of Nasal Nitric Oxide in the Resolution of Experimental Rhinovirus Infection," J. Allergy Clin, Immunol. Apr. 2004; 113 (4): 697-702.

* cited by examiner

NITRIC OXIDE UPPER AIRWAY DELIVERY SYSTEM AND METHOD

BACKGROUND OF THE INVENTION

The upper respiratory tract is a primary entrance port for microorganisms entering the lungs, i.e., the lower respiratory tract, of a subject. The upper respiratory tract frequently traps these microorganisms where they may be killed before they effectively enter the lungs. However, if a microorganism is able to survive in the upper respiratory tract, the microorganism may thereafter move into the lungs. Additionally, the existence or persistence of microorganisms, such as a virus, in the upper respiratory tract may lower the effectiveness of the subject's immune system, such that the lungs become susceptible to other microorganisms that may cause secondary infections, such as bacteria that may cause bacterial pneumonia or another type of infection. Additionally, the persistence of microorganisms in the sinuses can directly cause chronic headaches, cough and nasal discharge. Therefore, targeted therapeutic or preventative treatment of the upper respiratory tract can speed the recovery from local infections and/or prevent infection in the lungs or some other part of a subject's body.

The link between an upper respiratory tract infection and infection in the lower respiratory tract is well documented. For example, the following articles, each herein incorporated by reference in their entirety, support the proposition that treating the upper respiratory tract has beneficial value to the health of the lungs and lower respiratory tract. Papadopoulos, et al., "Rhinoviruses infect the lower airways." J. Infect. Dis. 2000; 181:1875-1884; Gern J. E., "Viral respiratory infection and the link to asthma.\," Pediatr. Infect. Dis. J. 2004; 23 (Suppl. 1):S78-S86; Fraenkel, et al., "Lower airway inflammation during rhinovirus colds in normal and in asthmatic subjects." Am. J. Respir. Crit. Care Med. 1995: 151:879-886; and Pizzichini, et al., "Asthma and Natural Colds. Inflammatory Indices in Induced Sputum: A Feasibility Study," Am J. Respir. Crit. Care Med. 1998; 158:1178-84.

The focus of treatment of the upper respiratory tract is often on traditional pharmaceuticals, such as oral antibiotics. In the 1980's, it was discovered that the endothelium tissue of the human body produced nitric oxide (NO), and that NO is an endogenous vasodilator, namely, an agent that widens the internal diameter of blood vessels and is also one of the basic elements of the human body's natural defense mechanisms against microorganisms. NO is most commonly known as an environmental pollutant that is a byproduct of combustion. However, it has been discovered that inhaled NO at low concentrations can be used to treat various pulmonary diseases in patients. For example, NO has been investigated for the treatment of patients with increased pulmonary artery resistance as a result of pulmonary arterial hypertension in both adults and children and is the primary treatment for "Blue Baby" syndrome. NO has also been shown to have anti-microbial and/or microcidal activity over a broad range of microorganisms.

While NO has shown promise with respect to certain medical applications, delivery methods and devices must address problems inherent with gaseous NO delivery. First, exposure to high concentrations of NO may be toxic, especially exposure to NO in concentrations over 1000 ppm. Even lower levels of NO, however, can be harmful if the time of exposure by the lungs is relatively high. For example, the Occupational Safety and Health Administration (OSHA) has set respiratory tract exposure limits for NO in the workplace at 25 ppm time-weighted averaged for eight hours.

Another problem with the delivery of NO is that NO rapidly oxidizes in the presence of oxygen to form $NO_2$, which is highly toxic, even at low levels. If the delivery device contains a leak, unacceptably high levels of $NO_2$ gas can develop. In addition, to the extent that NO oxidizes to form $NO_2$, there is less NO available for the desired therapeutic effect. The rate of oxidation of NO to $NO_2$ is dependent on numerous factors, including the concentration of NO, the concentration of $O_2$, and the time available for reaction. Since NO will react with the oxygen in the air to convert to $NO_2$, it is desirable to have minimal contact between the NO gas and the outside environment.

Systems have been developed to deliver NO to the upper respiratory tract without introduction into the lungs. For example, U.S. Pat. No. 8,043,252 describes a system of delivering NO to one nostril during patient exhalation against a positive pressure to close the soft palate. However, such a system is limited as it requires patients to exhale against a pressure that may be uncomfortable for breathing or may be difficult for some patients to perform, such as patients who have had strokes or who have less control of their breathing. This can thus limit the efficacy of delivered NO in the upper respiratory tract.

Accordingly, there is a need in the art for an improved device and method for the treatment of upper respiratory tract by the administration of gaseous NO, without allowing the introduction of NO to the lungs. The present invention satisfies this need.

SUMMARY OF INVENTION

The present invention relates to systems and methods for the delivery of nitric oxide to the upper respiratory system of a subject. In one embodiment, the system of the present invention is a nasal delivery system for delivering nitric oxide-containing gas to an upper respiratory tract of a subject, comprising: a source of nitric oxide-containing gas; a nasal interface adapted to provide fluid communication between the source of nitric oxide-containing gas and the nostrils of the subject; a flow-control valve for controlling the flow of the nitric oxide-containing gas from the source to the subject; and a flow sensor positioned near the oral cavity of the subject. In another embodiment, the system of the present invention is a nasal delivery system for delivering nitric oxide-containing gas to an upper respiratory tract of a subject, comprising: a source of nitric oxide-containing gas; a nasal interface adapted to provide fluid communication between the source of nitric oxide-containing gas and the nostrils of the subject; a flow-control valve for controlling the flow of the nitric oxide-containing gas from the source to the subject; and a means for operating the flow-control valve.

In one embodiment, the present invention is a method of delivering an effective amount of nitric oxide to the upper respiratory tract of a subject comprising the steps of: providing an embodiment of a nasal delivery system of the present invention; sensing the exhalation of the subject; and opening the flow control valve upon the sensing of exhalation, thereby delivering an effective amount of nitric oxide to the upper respiratory tract of the subject. In another embodiment, the present invention is a method of delivering an effective amount of nitric oxide to the central nervous system of a subject comprising the steps of: providing an embodiment of a nasal delivery system of the present invention; sensing the exhalation of the subject; and opening the flow control valve upon the sensing of exhalation, thereby delivering an effective amount of nitric oxide to the upper respiratory tract of the subject, wherein the nitric oxide bypasses the blood brain barrier and enters the central nervous system. In yet another embodiment, the present invention is a method of delivering an effective amount of nitric oxide to the upper respiratory tract of a subject comprising the steps of: providing an embodiment of a nasal delivery system of the present invention; and opening the flow-control valve immediately prior to or during exhalation, thereby delivering an effective amount of nitric oxide to the upper respiratory tract of the subject.

In one embodiment, the flow sensor of the present invention is operable to sense the exhalation of the subject. In another embodiment, the flow sensor comprises a sensor selected from the group consisting of a microphone, pressure sensor, mass flow sensors, Kapton flow sensors, and a thermistor. In yet another embodiment, the flow sensor is operably connected to the nasal interface. In one embodiment, the system is operable to deliver about 1 liter per minute of the nitric oxide-containing gas. In another embodiment, the system is operable to deliver a volume of nitric oxide containing gas, wherein the volume is between 1-1000 mL. In one embodiment, the means for operating the flow-control valve is a mechanical or electrical switch.

In various embodiments, the systems of the present invention may comprise other components. In one embodiment, the system comprises a control unit with logic such that the flow control valve is opened when exhalation is sensed by the flow sensor. In one embodiment, the system comprises a gas blender. In one embodiment, the system comprises a NO analyzer. In one embodiment, the nasal interface of the present invention comprises a nosepiece operable to be inserted into one or both of the nostrils of the subject.

In various embodiments, the methods of the present invention may comprise additional steps or features. In one embodiment, the method comprises predicting the onset of exhalation. In one embodiment, the method comprises closing the flow control valve before exhalation ceases. In one embodiment, the method decontaminates the upper respiratory tract of microorganisms. In one embodiment, the method treats or prevents an infection. In one embodiment, the method comprises predicting the onset of exhalation. In one embodiment, the method comprises closing the flow control valve before exhalation ceases. In one embodiment, the method is a treatment for a condition selected from the group consisting of stroke, brain injury, and migraine.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION

It is to be understood that the figures and descriptions of the present invention have been simplified to illustrate elements that are relevant for a clear understanding of the present invention, while eliminating, for the purpose of clarity, many other elements found in typical delivery systems and devices. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

The terms "patient," "subject," "individual," and the like are used interchangeably herein, and refer to any animal amenable to the systems, devices, and methods described herein. Preferably, the patient, subject or individual is a mammal, and more preferably, a human.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

Description

The present invention includes a device, system and method for the controllable delivery of nitric oxide (NO) to the upper airway of a subject without NO delivery to the lungs of the subject. The present invention can be used, for example, for decontamination of the upper respiratory tract with NO or for dilation of the cerebral vessels by NO. NO delivery to the upper respiratory tract can be used in various treatments including the treatment of diseases, disorders, or conditions including, but not limited to, bacterial infection, viral infection, stroke, brain injury, and migraines. In certain embodiments, the invention allows for delivery of NO through the nasal cavity into one or more paranasal sinus. As described herein, while NO has specific therapeutic benefits, it is important that NO is not delivered to the lungs, as it may, in certain instances, result in toxic or harmful effects on the subject.

The anatomy of a human's nasal airway can generally be described as follows. The nostrils are connected to two nasal cavities, or fossa, which are separated by the nasal septum. These nasal cavities are in communication with the nasopharynx, which is the upper part of the pharynx, or throat. A number of sinuses are also in communication with the nasal cavities, such as the frontal sinuses, paranasal sinuses, and maxillary sinuses. In addition, the nasal cavities comprise olfactory epithelium, i.e., the tissue responsible for detecting odors. The nasal airway can also communicate with the oropharynx and oral cavity. The soft palate, or oropharyngeal velum, can rise to separate the nasal airway from the oropharynx and oral cavity, for example during swallowing.

The devices and methods of the present invention provide delivery of nitric oxide to the upper respiratory tract. As used herein, the term "upper respiratory tract" is the space within the nasal cavities, sinuses, and nasopharynx, i.e., the area of the respiratory tract between the nostrils and the soft palate. Further, the device and methods of the present invention can be used to perform controlled nasal delivery of nitric oxide or a gas comprising nitric oxide. As described herein, controlled delivery refers to delivery of nitric oxide, or a gas comprising nitric oxide, to a subject, wherein the nitric oxide delivered is confined to the upper respiratory tract of the subject.

Controlled delivery of nitric oxide to the upper respiratory tract may be achieved by delivering nitric oxide specifically during exhalation. For example, the delivery of nitric oxide gas may be timed with a subject's exhalation. In one embodiment of the present invention, the delivery of NO may be triggered by sensing a subject's exhalation from the mouth. Upon sensing of the subject's exhalation, delivery of nitric oxide containing gas can then be made to the upper respiratory tract.

The present invention overcomes the limitations of prior systems that rely on other methods in an effort to perform controlled delivery of nitric oxide. The methods of such systems include: limiting the volume of gas delivered to the upper respiratory tract to only that of the volume of the upper respiratory tract; delivering the gas up the subject's nostrils near the end of the subject's inhalation; or delivering the gas to only one nostril during exhalation while inducing an increase in pressure that might seal the soft palate, thereby forcing the delivered gas out the other nostril. For example, the present invention does not require that the patient exhale against a positive pressure to close the soft palate. In addition, the present system provides increased NO contact time with the entire upper respiratory tract compared to prior systems, therefore enhancing the benefits of NO exposure.

By confining the delivery of NO to the upper respiratory system, the potential for toxicity is minimized when using the concentration of NO required for therapeutic applications. Since gas comprising NO does not reach the lungs in the systems and methods of the present invention, there is less absorption of the nitric oxide into the blood stream, thereby reducing the potential to form methemoglobin. Further, the potential for damaging the lungs as a result of the conversion of NO to $NO_2$ is also minimized. Conversely, previous delivery methods for gaseous NO allow a gas comprising NO to flow directly or indirectly into the lungs.

Accordingly, in the systems and methods of the present invention, NO concentrations greater than 100 ppm, and, more preferably, greater than 160 ppm may be used to safely bathe the upper respiratory tract of a subject. In various embodiments, the concentration of nitric oxide in the gas being delivered to the subject is about 120 ppm to about 400 ppm. In a preferred embodiment, the NO concentration is about 160 ppm to about 220 ppm.

In one embodiment of the present invention, gas comprising NO, i.e. NO-containing gas, may be nasally delivered to a subject during exhalation. While the subject exhales through the oral cavity, a flow-control valve is opened to administer the gas comprising NO from a nitric oxide gas source through one or both nostrils of the subject. For example, in one embodiment, the system senses expiratory flow, which triggers the delivery of NO into the nares and upper respiratory tract. In certain instances, the delivered NO spills into the lower nasopharynx. This gas flow will merge with the expiratory flow from the lungs and exit the mouth. The volume and time of NO flow is very small in comparison to the time and volume of the expiratory flow from the lungs. Thus, the greater lung flow will clear the oral cavity and, when the subject breathes back in on the next inspiration, all of the NO that had spilled into the nasopharynx will have exited the mouth. Accordingly, all of the inspired air is free of NO, and, therefore, no NO-containing gas will be inspired into the lungs.

The NO-containing gas exhaled through the mouth of the subject can be sent into the atmosphere. Because the volume of NO-containing gas is relatively small, e.g., about 1 liter per minute, allowing this gas to be sent freely into the atmosphere does not create a substantial risk of harm to the patient or to others in the surrounding environment. The ambient concentration of nitric oxide or nitrogen dioxide resulting from the use of the delivery system of the present invention is estimated to be about 50 ppb (parts per billion). By comparison, a similar volume of exhaled cigarette smoke typically contains about 150 ppm (parts per million) of NO. Therefore, allowing exhaled NO-containing gas to be sent into the atmosphere is significantly less harmful than the NO from cigarette smoke.

Figure 1:
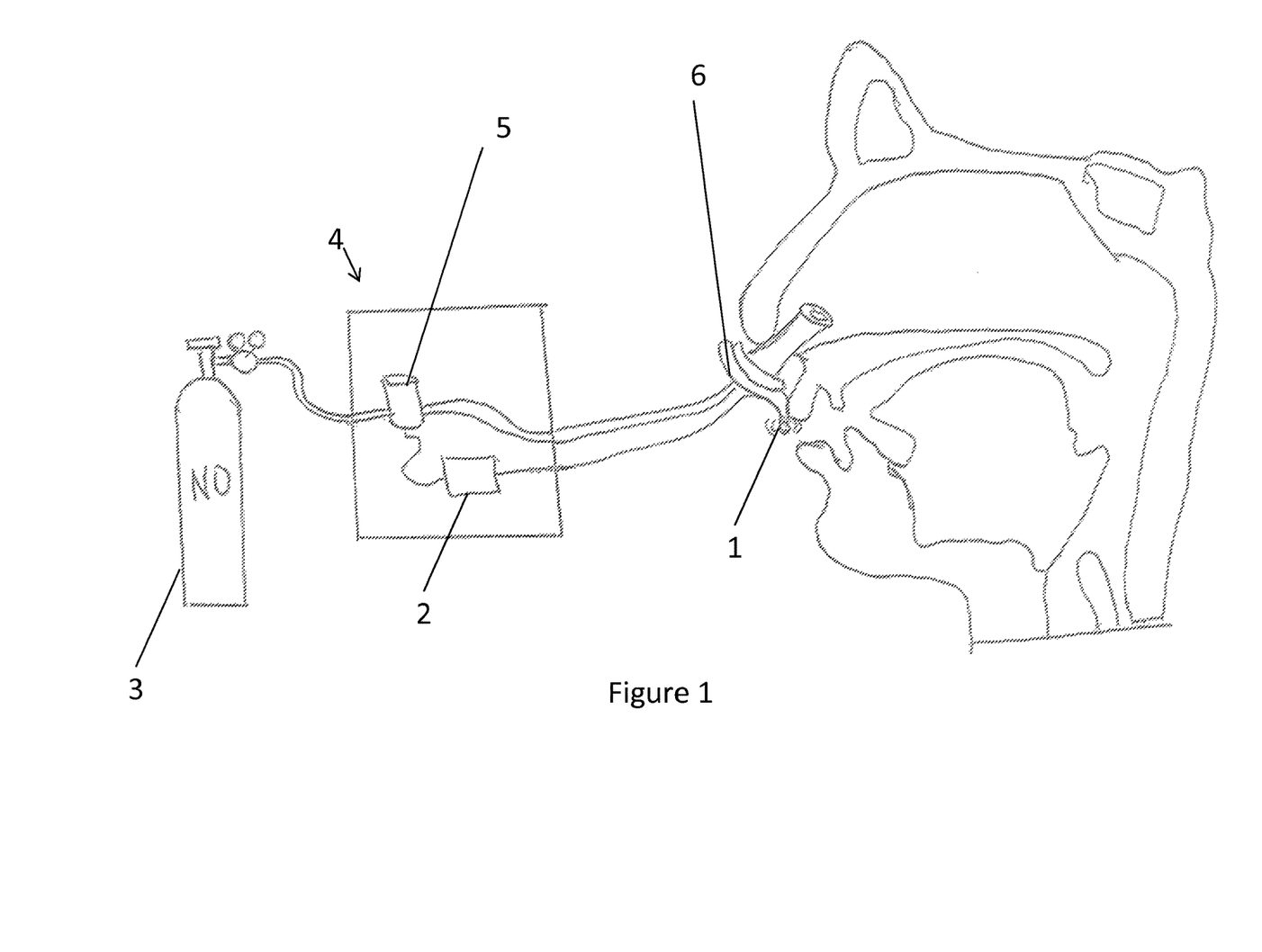
FIG. 1 is a schematic illustrating an exemplary system of the invention.

FIG. 1 depicts an exemplary system of the present invention, comprising flow sensor 1, NO gas source 3, control unit 4, and nasal interface 6. Flow sensor 1 senses exhalation of the subject, communicates the sensed exhalation to control unit 4, which triggers the release of NO from NO gas source 3, thereby delivering gas comprising NO through nasal interface 6 into the upper respiratory tract of the subject.

Flow sensor 1 may be any suitable sensor known in the art, which can be used to detect one or more parameters of subject exhalation. For example, flow sensor 1 may comprise a thermistor, pressure sensor, microphone, mass flow sensors, Kapton flow sensor or the like. Flow sensor 1 may be placed at or near the mouth of the subject through any suitable means. For example, flow sensor 1 may be adhered to the lip of the patient or held in place with supports over the ears of the subject. In one embodiment, flow sensor 1 is mounted onto nasal interface 6, as depicted in FIG. 1.

Referring again to FIG. 1, the NO gas source 3 may be a pressurized cylinder containing NO gas. Appropriate systems and methods for storing and using gas comprising NO, diluting the gas to effective concentrations, and channeling the gas to a delivery device are known in the art, and are described, for example, in U.S. Pat. Nos. 6,793,644 and 6,581,599, which are hereby incorporated by reference in their entirety. These systems and methods may be used with any delivery device described herein.

While the use of a pressurized cylinder is a preferred method of storing the NO-containing gas source, other storage and delivery means, such as a dedicated feed line can also be used. The NO can be produced at the device by chemical means as described in U.S. Pat. Nos. 7,220,393 or 7,939,045 or by conversion of $NO_2$ to NO as described in U.S. Pat. No. 7,560,076. The NO-containing gas may be adjusted for NO concentration by use of a diluent gas as described in U.S. Pat. No. 6,793,644 or the NO-containing gas may be supplied in its desired concentration without the need for dilution. The source of diluent gas may contain air, nitrogen, oxygen, an inert gas, or a mixture of such gases. The source of diluent gas may be stored within a pressurized cylinder or provided by a simple air pump. For example, compressed clean, dry air at 50 psig may be blended with the NO source gas. Both the NO gas source and the diluent source may include internal or external filters, such as a particulate filter, a water trap filter, or a combination thereof. Because the topically applied gas is not inhaled, it does not need to contain oxygen as one of its components.

The NO gas from the NO gas source 3 and the diluent gas from the diluent gas source preferably pass through pressure regulators to reduce the pressure of gas that is admitted to the control unit 4 and delivered to the subject. The respective gas streams may also pass via tubing to an optional gas blender to mix the respective gases. The NO-containing gas may be output from the gas blender and travel via tubing to a flow control valve 5, preferably contained in the control unit 4. Flow control valve 5 may include, for example, a proportional control valve that opens or closes in a progressively increasing, or decreasing if closing, manner. As another example, flow control valve 5 may include a mass flow controller.

In one embodiment, control unit 4 further comprises sensor electronics unit 2, which is operably connected with flow sensor 1. Sensor electronic unit 2 comprises hardware components suitable to send and receive information regarding the exhalation of the subject, as sensed by flow sensor 1. In certain embodiments, sensor electronic unit 2 stores data in relation to the timing of exhalation, as sensed by flow sensor 1. Sensor electronic unit 2 provides appropriate signals for the opening and closing of flow control valve 5 to trigger release of NO. Flow control valve 5 controls the flow rate of the NO-containing gas that is introduced to the nasal interface 6. The NO-containing gas leaves flow control valve 5 via flexible tubing. The flexible tubing attaches to an inlet in the nasal interface 6. The triggering event for opening the flow of NO-containing gas to the nasal interface 6 occurs when flow sensor 1 and sensor electronic unit 2 determine that that exhalation is occurring or is predicted to occur. The identification of exhalation may be determined by changing in flow direction, increasing temperature that reflects warm air or higher pressures as with a pitot sensor, or by similar methods as defined by the sensor technology.

In one embodiment, control unit 4 is computer controlled via a controller such as a microprocessor. However, discrete electronic or pneumatic components could accomplish the same objective. Logic (either through firmware or software) may be programmed in order to control the delivery of NO such that delivery of NO gas from NO gas source 3 is triggered when exhalation is sensed by flow sensor 1.

In one embodiment, delivery of nitric oxide gas to the upper respiratory tract may be achieved through delivery that is coincidental with the exhalation of the subject. The inspiration and expiration flow rates of a spontaneous breathing of a patient may be monitored using flow sensor 1 and, inspiration and expiration flow profiles can be determined for the subject's breathing. Nasal delivery of the NO-containing gas may be timed to coincide with the subject exhalation.

Alternative triggering of the NO flow into the breathable gas stream can also be accomplished by measuring and modeling the patient's exhalation profile for a number of previous breaths. NO flow is then initiated on a subsequent exhalation based upon a predicted timing of the patient's breathing to flow NO only during exhalation so that NO is delivered and exhaled during the exhalation, thereby preventing NO delivery to the lungs. In certain embodiments, the timed NO delivery is preferably performed through the use of control unit 4, as previously described, that may time the release of the nitric oxide containing gas to the nasal interface. The timing may be during exhalation, or at a predetermined time based upon measurements of prior breathing patterns. In any timed delivery, the volume of NO-containing gas is about equal to the patient's nasal cavity. This volume may be monitored or adjusted based on successive breaths.

In another embodiment, a pulse dose delivery or a bolus injection delivery of the NO-containing gas may be used. The timing of the bolus injection may be correlated to the detection of the subject's breath. Once a predetermined time period has passed following breath detection, a bolus injection of the NO-containing gas may be delivered to the upper respiratory tract of the subject. The nasal delivery of the NO-containing gas may be "artificial" or forced, such as delivered through a pressurized system through the nostril(s) into the upper respiratory tract. The volume and timing of delivered NO-containing gas ensures that NO does not flow down to the lungs. Hence, through the targeted delivery of the NO-containing gas, the NO-containing gas will only bathe and contact the upper respiratory system of the subject. Accordingly, there is little or no risk that the NO-containing gas will reach beyond the nasopharynx into the lungs of the subject.

In another embodiment, the triggering of the bolus injection delivery can be performed manually by either the subject or a second person to coincide with the subject's exhalation. The trigger for such manual delivery can be an electric or mechanical switch, or some other means of triggering the opening of a valve, as would be understood by a person skilled in the art. In such an embodiment, the subject or another person can manually trigger the opening of the valve immediately prior to, at the same time as, or immediately after, the start of exhalation, thereby delivering a therapeutically effective amount of NO-containing gas to the upper respiratory tract of the subject.

Additionally, NO and $NO_2$ analyzers, which are known in the art, may also be incorporated into the control unit 4 to monitor the NO and $NO_2$ concentration of the gas delivered to the subject's upper respiratory tract.

The nasal interface 6 may include one or two nasal insert prongs that fit into one or both of the nostrils of the patient, providing a tight sealing fit. The nasal insert prongs may be oval or cylindrical in shape, may include a flange design to hold the insert within the nostril, and may be shaped to fit coaxially within the nostril of a patient. Such a suitable nasal insert prong may be the nasal inserts described for use in the treatment of obstructive sleep apnea syndrome with continuous positive airway pressure (CPAP) devices. An appropriate nasal interface is one that is made of a soft, flexible material and provides an effective sealing of the nostril. In addition to insert prongs, a nasal pillow of other suitable design may be used. The nasal interface 6 may be formed of a resilient material such as a polymeric or silicone elastomer material. The nasal interface 6 may include an optional one-way valve that prevents the backflow of gas into the tubing.

Figure 2:
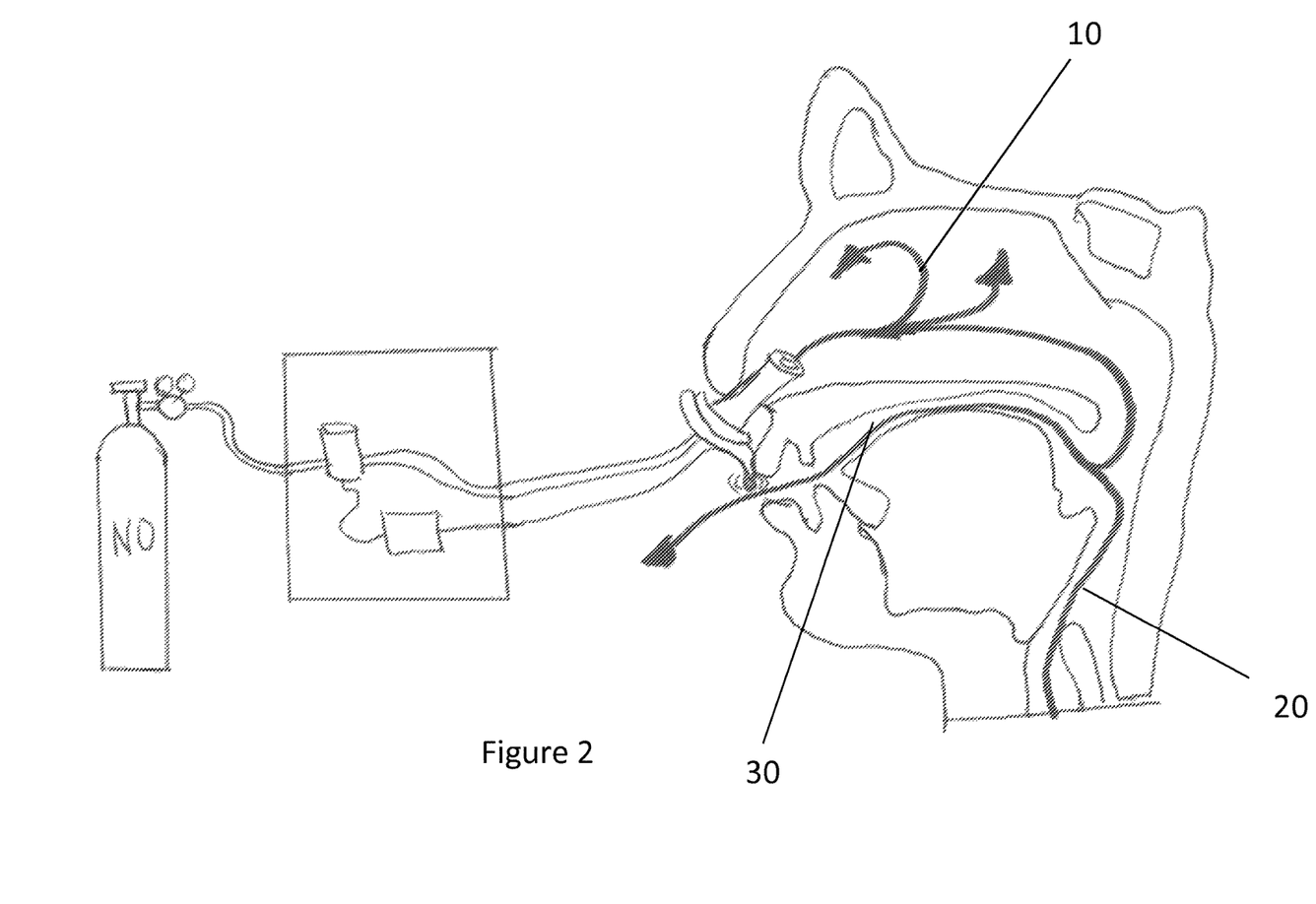
FIG. 2 is a schematic illustrating the delivery of NO during exhalation.
Figure 3:
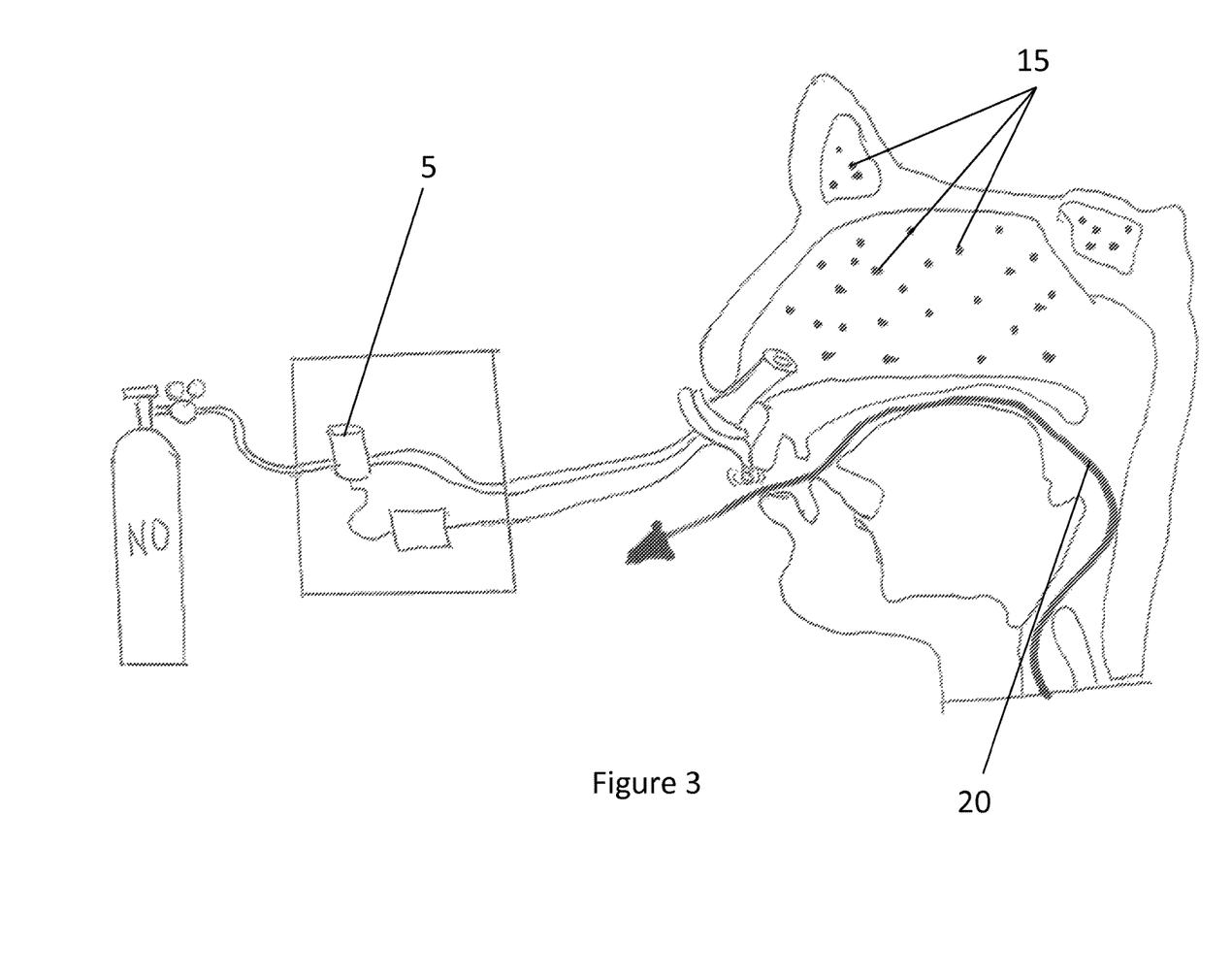
FIG. 3 is a schematic illustrating the molecules of nitric oxide remaining in the upper airway while the oropharynx is cleared during continued exhalation which follows cessation of NO flow.

As depicted in FIG. 2, delivery of NO during exhalation, denoted as 10, results in the spillover of delivered NO to mix with expiratory flow 20 from the lungs. The combination 30 of the delivered NO 10 and lung expiratory flow 20 is then expired out of the oral cavity. As depicted in FIG. 3, following the cessation of NO flow from valve 5, residual NO molecules 15 can remain in the nasal cavity or sinuses while the oral cavity is cleared of any NO gas during the continued exhalation 20. These residual NO molecules can increase the effectiveness of the NO treatment by increasing the amount of NO contact time in the upper respiratory tract, but they will not create the potential for significant adverse health effects to the subject. If any of the residual NO molecules 15 migrate into the nasopharynx or pharynx after delivery, they will be immediately flushed from the oral cavity via the expiratory flow 20. This results in complete or near-complete exhalation of the delivered NO via the mouth. Any gas subsequently inhaled into the lungs, therefore, will contain little to none of the NO delivered during the previous exhalation event. Thus, the potential for a significant adverse health effect caused by inhalation of NO gas is minimized or eliminated by the exhalation NO delivery mechanism of the present invention.

Therapeutic Treatments Using Delivery of NO Gas

In one embodiment, the present invention provides a method for treating a disease, disorder, or condition associated with microbial contamination of the upper respiratory tract or paranasal sinus. The delivery of a NO containing gas nasally to an upper respiratory area of a subject may topically decontaminate the upper respiratory tract or paranasal sinus of microorganisms, such as viruses, bacteria, mycobateria, parasites, and fungi. This decontamination may be an effective treatment of sinus infections, nasopharyngeal infections and upper respiratory infections. For example, as depicted in FIG. 3, delivery of NO via the system of the invention would result in the delivery of NO into the paranasal sinuses of the subject, which may be beneficial in reducing or eliminating infection of the sinuses.

Suitable therapeutic volumes of NO containing gas may be delivered to a subject. For example, a total gaseous flow rate may be about 1 liter per minute to about 2 liters per minute. For example, if NO is first blended with air, the NO gas flowing from the NO gas source may be about 0.2 liter per minute, while the compressed air flow may be about 0.8 liter per minute. Since the injection of NO-containing gas to the nasal interface is controllably timed to correlate with an exhalation event, the flow rate of about 1 liter per minute may not be a continuous flow rate, but rather represents the rate of the pulsed injection. Each pulse injection therefore, may last for about 1 to about 5 seconds. The injections may also be consecutive for about 3 to about 60 minutes. In one embodiment, the flow of NO is delivered, as appropriate as described herein, until a specific volume of NO-containing gas is delivered to the upper respiratory tract. Such volumes include, for example 10 mL, 30 mL, 1000 mL, or the like.

The NO-containing gas may be dosed in several ways to supply a therapeutic amount. The term "therapeutic amount," refers to an amount sufficient to kill or inhibit microorganisms in the upper respiratory tract. A flow rate of about 1 liter per minute of a gas comprising about 160 ppm to 400 ppm nitric oxide may effectively decontaminate the upper respiratory tract of a subject. Other suitable parameters for delivery, dosage, or NO exposure may be found in U.S. Pat. Nos. 6,793,644 and 6,432,077. In any delivery method, NO containing gas may be by bolus injection, or by pulse injection, systematically, for a period of time. Suitable exposure times may be, for example, about 3 minutes to about 60 minutes of total NO exposure time.

While the delivery of the NO containing gas is isolated to the upper respiratory system, including the nasopharynx, the decontamination of the upper respiratory tract of microorganisms provides an effective treatment of sinus infections and greatly reduces risk of the spreading of infection to the lower respiratory tract and provides a preventative treatment of the respiratory system as a whole, including the lungs.

The dominant mechanism(s) whereby NO, which is known to be produced in response to stimulation of the calcium-independent inducible nitric oxide synthase, results in intracellular killing of mycobacteria has been described in the scientific and patent literature (Miller et al., 2007, Antimicrobial Agents and Chemotherapy, 51(9); 3364-66; U.S. patent application Ser. No. 09/762,152). Additionally, viruses may be susceptible to nitric oxide. For example, viruses may be susceptible to nitric oxide due to their unsophisticated detoxification pathways. Several possible mechanisms exist to explain the cidal and inhibitory effects of NO on viruses. First, metal ion-based DNA deamination may be linked to the cidal effectiveness of NO. NO may also play a dominant role in destructive hydroxyl radical formation. Further, NO may interfere with viral replication through RNA reductase inhibition; NO may interfere with Hemagglutinin protein synthesis; and NO may interfere with virion release or maturation.

The antiviral effects of the NO molecule produced chemically by NO donors has been well documented. For example, cells infected with influenza virus A/Netherlands/ 18/94 were treated with NO, an experiment described in Rimmelzwaan, et. al., "Inhibition of Influenza Virus Replication by Nitric Oxide," J. Virol. 1999; 73:8880-83, herein incorporated by reference in its entirety. Results show the effectiveness of NO as a preventive therapy to viral agents. Additionally, a study by Sanders, et. al. demonstrates the effectiveness of naturally produced NO by the body as an antiviral agent, particularly against human rhinovirus. See Sanders, et. al., "Role of Nasal Nitric Oxide in the Resolution of Experimental Rhinovirus Infection," J. Allergy Clin, Immunol. 2004 April; 113(4):697-702, herein incorporated by reference in its entirety.

In one embodiment, the present invention includes methods of delivering NO to the central nervous system (CNS) through the nasal cavity. The nasal cavity has recently emerged as an effective route to delivery drugs and pharmaceutical agents to the brain by bypassing the blood brain barrier (Rodriguez and Teste, 2009, The Scientific World Journal, 9: 970-981). Nitric oxide is a known vasodilator, which can thereby dilate blood vessels in the CNS and increase blood flow. Thus, nitric oxide delivery by way of the present invention can be used to treat CNS disorders, including stroke, traumatic brain injury, headaches, migraines, and the like. For example, targeted NO delivery to the upper respiratory tract can induce NO delivery to appropriate regions in the CNS, where NO can exert its beneficial effects. Importantly, as described herein, the delivery method does not result in NO delivery to the lungs. Thus, the present invention includes safe delivery of NO to the CNS for the treatment of such disorders.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A nasal delivery system for delivering nitric oxide-containing gas to an upper respiratory tract of a subject, comprising:
   a source of nitric oxide-containing gas;
   a nasal interface adapted to provide fluid communication between the source of nitric oxide-containing gas and the nostrils of the subject;
   a flow-control valve for controlling the flow of the nitric oxide-containing gas from the source to the subject;
   a flow sensor positioned near the oral cavity of the subject; and
   a control unit in communication with the flow-control valve and the flow sensor;
   wherein the control unit is configured to allow delivery of nitric oxide-containing gas to the upper respiratory tract while the soft palate of the subject is open during exhalation of air.

2. The system of claim 1, wherein the flow sensor is operable to sense the exhalation of the subject.

3. The system of claim 1, wherein the flow sensor comprises a sensor selected from the group consisting of a microphone, pressure sensor, mass flow sensors, Kapton flow sensors, and a thermistor.

4. The system of claim 1, wherein the flow sensor is operably connected to the nasal interface.

5. The system of claim 1, wherein the nasal interface comprises a nosepiece operable to be inserted into one or both of the nostrils of the subject.

6. The system of claim 1, wherein the system comprises a control unit with logic such that flow control valve is opened when exhalation is sensed by the flow sensor.

7. The system of claim 1, further comprising a gas blender.

8. The system of claim 1, further comprising a NO analyzer.

9. The system of claim 1, wherein the system is operable to deliver about 1 liter per minute of the nitric oxide-containing gas.

10. The system of claim 1, wherein the system is operable to deliver a volume of nitric oxide containing gas, wherein the volume is between 1-1000 mL.

11. A method of delivering a therapeutic amount of nitric oxide to the upper respiratory tract of a subject comprising the steps of:
   providing the system of claim 1;
   sensing the exhalation of the subject; and
   delivering a therapeutic amount of nitric oxide to the upper respiratory tract of the subject.

12. The method of claim 11, wherein the method comprises predicting the onset of exhalation.

13. The method of claim 11, wherein the method comprises closing the flow control valve before exhalation ceases.

14. The method of claim 11, wherein the method decontaminates the upper respiratory tract of microorganisms.

15. The method of claim 11, wherein the method treats or prevents an infection.

16. A method of delivering a therapeutic amount of nitric oxide to the central nervous system of a subject comprising the steps of:
   providing the system of claim 1;
   sensing the exhalation of the subject; and
   delivering a therapeutic amount of nitric oxide to the upper respiratory tract of the subject, wherein the nitric oxide bypasses the blood brain barrier and enters the central nervous system.

17. The method of claim 16, wherein the method comprises predicting the onset of exhalation.

18. The method of claim 16, wherein the method comprises closing the flow control valve before exhalation ceases.

19. The method of claim 16, wherein the method is a treatment for a condition selected from the group consisting of stroke, brain injury, and migraine.

20. A nasal delivery system for delivering nitric oxide-containing gas to an upper respiratory tract of a subject, comprising:
   a source of nitric oxide-containing gas;
   a nasal interface adapted to provide fluid communication between the source of nitric oxide-containing gas and the nostrils of the subject;
   a flow-control valve for controlling the flow of the nitric oxide-containing gas from the source to the subject;
   a means for operating the flow-control valve; and
   a control unit in communication with the flow-control valve and the means for operating the flow-control valve;
   wherein the control unit is configured to allow delivery of nitric oxide-containing gas to the upper respiratory tract while the soft palate of the subject is open during exhalation of air.

21. The system of claim 20, wherein the means for operating the flow-control valve is a mechanical or electrical switch.

22. A method of delivering a therapeutic amount of nitric oxide to the upper respiratory tract of a subject comprising the steps of:
   providing the system of claim 20; and
   opening the flow-control valve during exhalation, thereby delivering a therapeutic amount of nitric oxide to the upper respiratory tract of the subject.

* * * * *